United States Patent [19]

Loebig

[11] Patent Number: 5,265,463
[45] Date of Patent: Nov. 30, 1993

[54] APPARATUS FOR MEASURING THE TRANSMISSION RATE OF VOLATILE ORGANIC CHEMICALS THROUGH A BARRIER MATERIAL

[75] Inventor: Craig Loebig, Elk River, Minn.

[73] Assignee: Modern Controls, Inc., Minneapolis, Minn.

[21] Appl. No.: 920,098

[22] Filed: Jul. 24, 1992

[51] Int. Cl.$^5$ ............................................. G01N 15/08
[52] U.S. Cl. ............................................. 73/38; 73/23.2
[58] Field of Search ................................. 73/38, 23.2

[56] References Cited

U.S. PATENT DOCUMENTS

| | | | |
|---|---|---|---|
| 3,498,110 | 3/1970 | Brun | 73/38 |
| 3,590,634 | 7/1971 | Pasternak et al. | 73/38 X |
| 3,604,246 | 9/1971 | Toren | 73/38 |
| 3,926,561 | 12/1975 | Lucero | 73/38 X |
| 4,091,655 | 5/1978 | French et al. | 73/23.2 |
| 4,656,865 | 4/1987 | Callan | 73/38 |
| 4,660,411 | 4/1987 | Reid | 73/38 |

FOREIGN PATENT DOCUMENTS

| | | | |
|---|---|---|---|
| 1045083 | 9/1983 | U.S.S.R. | 73/38 |
| 1631363 | 2/1991 | U.S.S.R. | 73/38 |

Primary Examiner—Hezron E. Williams
Assistant Examiner—Joseph W. Roskos
Attorney, Agent, or Firm—Palmatier, Sjoquist & Helget

[57] ABSTRACT

A system for measuring the transmission rate of volatile organic chemicals through a barrier material, where a barrier material sample is clamped in a test cell so as to form a chamber on both sides of the material, with a temperature-controlled test gas conveyed into one chamber and a temperature-controlled carrier gas conveyed through the other chamber. The carrier gas is passed through a cryotrap where the organic chemicals are collected, and the carrier gas with collected chemicals is then burned in a flame ionization detector to measure the quantity of organic chemicals.

13 Claims, 6 Drawing Sheets

APPARATUS FOR MEASURING THE TRANSMISSION RATE OF VOLATILE ORGANIC CHEMICALS THROUGH A BARRIER MATERIAL

BACKGROUND OF THE INVENTION

The present invention relates to a testing system for detecting and measuring the transmission rate of certain volatile organic chemicals through a barrier material, such as a thin plastic film.

The measurement of the rate of permeation of certain selected gases through film material is known in the art. For example, measurement of the permeation rate of oxygen through plastic film materials has been accomplished by various products manufactured by the assignee of the present invention. Oxygen permeation measuring systems typically utilize an oxygen sensor of the type described in U.S. Pat. No. 3,223,597, Hersch, which are uniquely capable of sensing minute quantities of oxygen in a carrier gas, and developing an electrical signal proportional to the quantity of oxygen sensed. Detectors of this type are generally known as coulometric sensors; while extremely useful for measuring quantities of gases such as oxygen, they are not usable for detecting quantities of organic materials conveyed by gaseous transmission.

The measurement of organic chemicals conveyed in gases can be accomplished by the use of a flame ionization detector, particularly when the substance to be measured produces charged ions when burned in a hydrogen-air flame. The combustion forms ions and free electrons which may be detected by electrodes placed in the flame ionization detector. A high voltage potential is imposed across the electrodes, which are spaced apart to form a gap, and the free ions and electrons lower the resistance across the gap and causes a current to flow. This current flow is measured as a voltage drop across an external resistor; the voltage drop is amplified and interpreted by an electrometer to provide a voltage representative of the characteristics of the gas. For example, when $CH_2$ chemical compositions are introduced into the flame a complex process takes place in which positively-charged carbon ions and electrons are formed, and the measured current is significantly increased in response to the additional ions and electrons. In an organic compound the electrical response is proportional to the number of oxidizable carbon atoms, and therefore can provide a measure of the type of organic compound. For example, butane has twice as many carbon atoms as an equivalent volume of ethane.

The flame ionization detector is insensitive to chemical compositions having fully oxidized carbons, such as carbonyl or carboxyl groups and ethers. The flame ionization detector does not respond to inorganic compounds apart from those easily ionized in a hydrogen/air flame at a relatively high temperature. It is also insensitive to water and permanent gases such as CO, $CO_2$, $CS_2$, $SO_2$, $H_2S$, $NH_3$, $N_2O$, NO, $NO_2$, $SiF_4$, and $SiCl_4$. Therefore, the flame ionization detector is particularly useful when it is required to measure small traces of organic materials borne by such permanent gases.

The flame ionization detector is a mass flow detector, and its performance varies with the flow rate of a carrier gas, the voltage applied across the detector electrodes, and the temperature of the flame. The temperature of the flame is a function of the hydrogen/air mix ratio. The detection limits for a flame ionization detector are about 5 nanograms (ng) per second for light hydrocarbon gases, increasing to about 10 ng per second for higher organic liquids and gases, and the response is linear over approximately seven orders of magnitude.

In the prior art, the accepted techniques for determining the quantity of organic chemicals conveyed by gases have been either by using a gas chromatograph or by gravimetric means where a weighing process is used. Such techniques usually involve determining not only the quantity of organic chemicals present in a gas, but also identifying the type of organic chemical.

It would be an advantage to have a system for detecting and measuring the quantity of known organic chemicals conveyed by gases, utilizing the principles of the flame ionization detector, wherein all of the variables affecting the detection and measurement process can be carefully controlled, including the temperatures of the various gases required in the process.

It is a principal object and advantage of the present invention to provide an apparatus for measuring the transmission rate of certain volatile organic chemicals through a barrier material. Examples of such volatile organic chemicals may be acetic acid, ethanol, methanol, pentane, propane, and xylene.

It is a further object and advantage of the present invention to provide an apparatus for testing the permeability of membranes relative to various volatile organic chemicals.

It is a further object and advantage of the present invention to provide a standardized measuring system whereby membrane permeability to volatile organic chemicals may be tested and classified.

The foregoing and other objects and advantages will become apparent from the following specification and claims, and with reference to the drawings.

SUMMARY OF THE INVENTION

A system for accepting a test gas and a carrier gas, wherein the test gas conveys a volatile organic chemical. The two gases are conveyed into a test cell separated into two chambers by a membrane material, wherein permeability through the membrane causes the volatile organics to be picked up by the carrier gas. The carrier gas is conveyed via temperature-controlled paths to an oven and cryotrap, and then to a flame ionization detector. The temperatures of the system are monitored and controlled by a computer processing system, and the electrical signal derived by the flame ionization detector electrometer is measured and analyzed in the data processing system to provide an output indicative of the permeability of the membrane to the volatile organics passing therethrough.

DESCRIPTION OF THE PREFERRED EMBODIMENT

Figure 1:
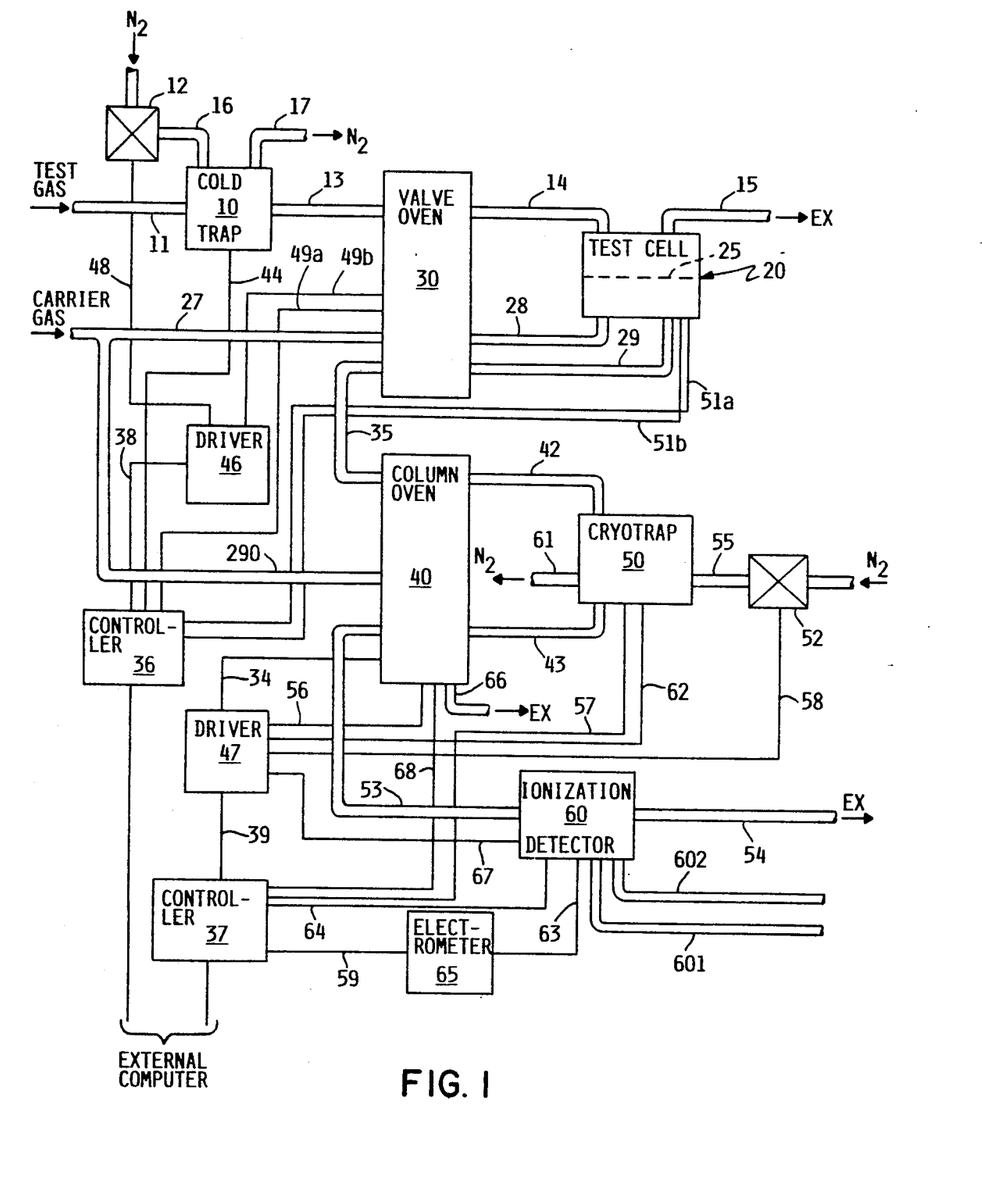
FIG. 1 is a block diagram showing the principal elements and flow paths of the present invention.

Referring first to FIG. 1, there is shown an overall block diagram of the invention. A test gas, which in general may be any organic gas that produces charged ions when burned in a hydrogen/air flame, is introduced into cold trap 10 via a gas line 11. The cold trap 10 protects the overall system from contamination by removing any water vapor present in the gas, as well as ensuring that the vapor pressure of the test gas is below 0° C. This prevents condensation of test gas in the system plumbing. The cold trap is cooled by conveying liquid nitrogen via a valve 12 and conduit 16 into the cold trap, and venting nitrogen gas out of the cold trap via conduit 17. The test gas emerges from cold trap 10 via gas line 13 at a predetermined and controlled temperature, and is fed into a valve oven 30. The test gas emerges from valve oven 30 in gas line 14 and passes into test cell 20. Provision is made for the exhaust (Ex) of the test gas from test cell 20 via gas line 15 after the gas has become expended. A membrane 25 separates test cell 20 into two chambers, and a heated carrier gas such as helium or nitrogen is fed through the lower chamber. The carrier gas is preferably purified helium. The carrier gas passes through a gas line 27 into the valve oven 30 where it is heated to approximately 100° C., and from there it is fed into the test cell 20 via a gas line 28; the carrier gas is removed from test cell 20 and recirculated through valve oven 30 via gas line 29 and into a column oven 40 via a heated line 35. Typically, at least a quantity of test gas permeates the membrane in the test cell 20 and is picked up by the carrier gas, including a quantity of the organic chemical found within the test gas.

The carrier gas with an organic content may be connected into cryotrap 50 via gas line 42 during the collection portion of a test cycle. The organic content in the gas is deposited in the cryotrap 50, and the carrier gas is connected back into column oven 40 via gas line 43, and is then exhausted via line 66. The organics collected in cryotrap 50 are conveyed to flame ionization detector 60. The output from flame ionization detector 60 may be coupled to a suitable exhaust reservoir via gas line 54. The carrier gas may also be exhausted into a suitable exhaust reservoir from column oven 40, via line 66, which is typically accomplished during the examination portion of a test cycle.

Pure carrier gas may also be directly fed into column oven 40 via gas line 290, where it may be exhausted into a surface exhaust reservoir via gas line 66, typically during a collection portion of a test cycle. Alternatively, pure carrier gas from gas line 290 may be connected into cryotrap 50 via gas line 42, as during the examination portion of a test cycle, wherein any organics collected in the cryotrap 50 during the collection portion of the test cycle are picked up by the carrier gas and conveyed back into the column oven 40 via line 43, and thereafter passed to flame ionization detector 60 via gas line 53. The organic content of the gas is burned in the flame ionization detector 60, and the remaining carrier gas is then coupled to a suitable exhaust reservoir via line 54. In addition to the carrier gas with organic content which is fed into flame ionization detector 60, certain other gases are required by the flame ionization detector in order to support the burning process. For example, hydrogen gas and air are supplied into flame ionization detector 60 via lines 601 and 602.

The gases in these lines support and control the flame in the detector, and the combustion products of these gases are exhausted into the exhaust register via line 54. The various gas passages through column oven 40 will be described with more particularity with reference to FIG. 5 herein.

The temperature of cold trap 10 is controlled by passing liquid nitrogen ($N_2$) through the cold trap housing. Liquid nitrogen is coupled through a valve 12 and a nitrogen flow line 16 into cold trap 10, and is circulated out from cold trap 10 via flow line 17, wherein the rate of flow is controlled by electrical control signals applied to valve 12 via control line 48 from driver module 46. Other temperatures of the components hereof are similarly controlled, in a manner to be described.

A controller 36 is suitably programmed to provide the control and monitoring functions hereinafter described. Controller 36 may communicate via its input-output (I/0) channels with an external computer, and also communicates via a plurality of lines 38 with driver 46. Driver 46 contains interface circuitry required for generating control signals to devices such as cold trap solenoid valve 12, valve oven 30, test gas valve 302 (see FIG. 3), and calibration valve 310. Controller 36 also receives electrical signals representative of temperatures being monitored throughout portions of the system. For example, controller 36 monitors the temperature of cold trap 10 by means of an internal temperature sensor and electrical signals generated over line 44. Controller 36 also monitors the temperature of valve oven 30 and generates control signals to driver 46 via lines 38, for purposes of maintaining a controlled temperature therein. Controller 36 also monitors the temperature of test cell 20 via lines 51a and 51b.

A controller 37 is suitably programmed to provide the control and monitoring functions hereinafter described with reference to driver 47. Controller 37 may communicate via its input-output (I/O) channels with an external computer, and also may communicate via a plurality of lines 39 with driver 47. As a result of the I/O channel connections, both of the controllers 36 and 37 may be externally controlled by a remote computer, and may be used to provide data for reports concerning the results achieved by the system to a remote computer. For example, the results of gas testing done by the system could be reported to and accumulated by a remote computer, which could subsequently provide management reports and historical reports concerning testing activities over an extended period of time.

Controller 37 monitors the electrometer 65 via line 59. Electrometer 65 is connected to the flame ionization detector 60 via line 63. Controller 37 also monitors the temperature of the flame ionization detector 60 by means of temperature sensor 546, via line 64. Controller 37 also monitors the temperature of cryotrap 50, utilizing temperature sensor 536 and line 57; controller 37 also monitors the temperature of column oven 40 with temperature sensor 526 via line 68. Controller 37 also sends appropriate signals to driver 47 for adjusting control elements so that a closed loop control over system temperatures may be maintained. Driver 47 may also control the test cycle sequencing via signals received from column oven 40.

Driver 47 controls the temperature of column oven 40 via an electric heater 525, and signals sent over lines 56. Likewise, driver 47 controls the cryogenic temperature of cryotrap 50 by the flow of liquid nitrogen through valve 52, which is electrically controlled by signals on line 58. Liquid nitrogen may flow into cryotrap 50 via gas line 55, and is exhausted from cryotrap 50 via gas line 61. Driver 47 controls the internal ambient temperature of cryotrap 50 by an electric heater (not shown) and signals on line 62.

Figure 2:
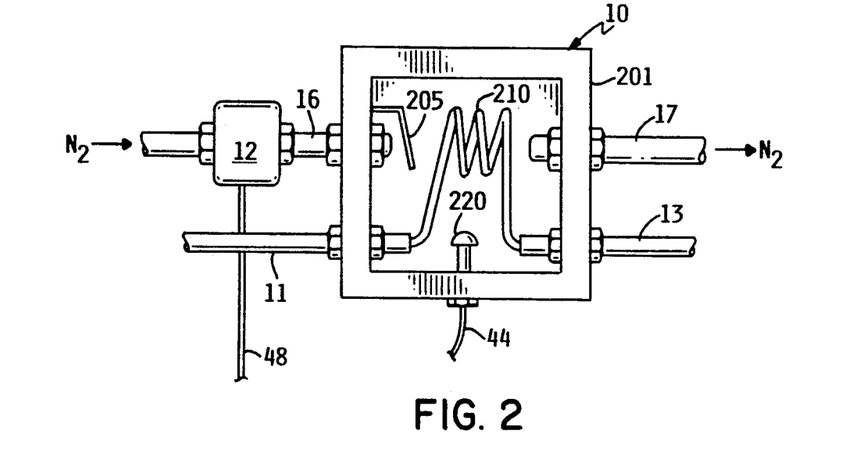
FIG. 2 shows the cold trap of the present invention.

Referring next to FIG. 2, the cold trap 10 is shown in cross-sectional view. Cold trap 10 comprises an outer sealed housing 201, including an inner and outer wall having a suitable thermal insulation therebetween. Liquid nitrogen is admitted into the interior of housing 201 via solenoid valve 12 and flow line 16. A deflector plate 205 is placed adjacent the flow line 16 entry point, to defuse the flow of liquid nitrogen into the interior of housing 201. Liquid nitrogen is removed from housing 201 via flow line 17. The rate of flow of liquid nitrogen into housing 201 is controlled by control signals transmitted via line 48, to open and/or close solenoid valve 12 A test gas is passed into cold trap 10 via gas line 11, which is coupled to an interior coil 210. The gas flows through coil 210 and thence out of cold trap 10 via gas line 13. A temperature sensor 220 is mounted inside housing 201, and the signal generated by temperature sensor 220 is applied to line 44, for subsequent coupling to controller 36. As the gas flows through coil 210 it releases heat into the liquid nitrogen which fills the interior of housing 201, thereby cooling the gas to a temperature which is below atmospheric. The gas temperature may be controlled by controlling the flow rate of liquid nitrogen through housing 201. In the preferred embodiment, the temperature of the gas which passes through cold trap 10 is kept between $-5°$ C. and $+5°$ C.

Figure 3:
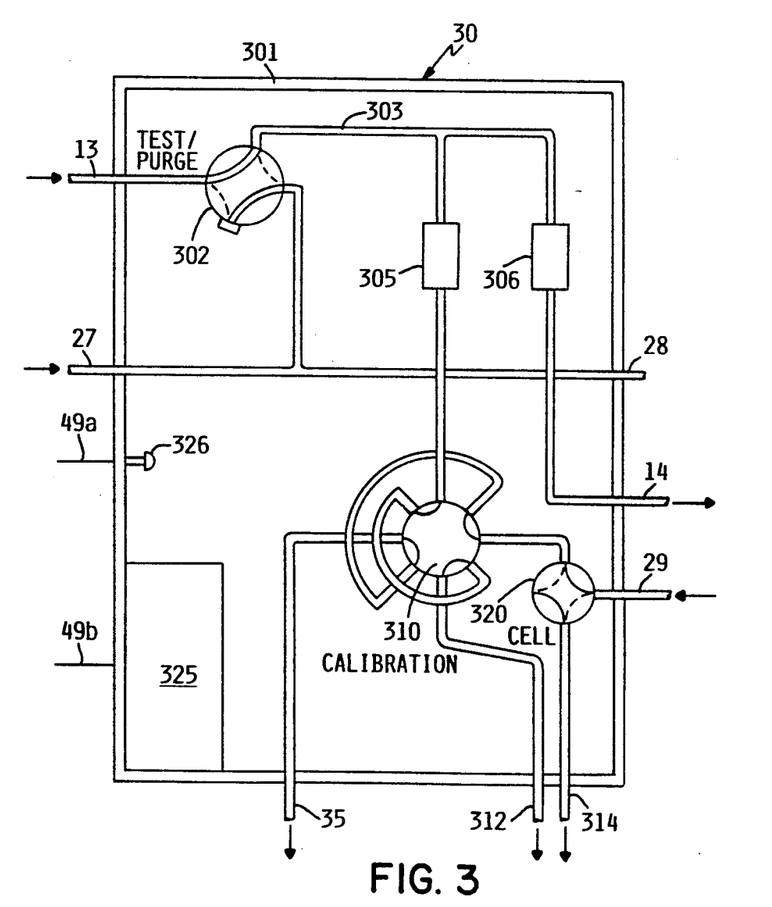
FIG. 3 shows the valve oven of the present invention.

FIG. 3 shows a more detailed diagram of valve oven 30, illustrating the interior valves and flow lines. Valve oven 30 is heated by a suitable electrical heater 325 wherein the temperature is controlled by the voltage applied to electrical line 49b, connected to driver 46. The exterior walls 301 are insulated to limit the escape of heat from valve oven 30. Carrier gas is introduced into the valve oven 30 via line 27, and passes away from valve oven 30 via line 28, to test cell 20. Test gas may be introduced into valve oven 30 via gas line 13, or carrier gas may be introduced into valve oven 30 via gas line 27. Both of these lines are connected to a test/purge valve 302 which may be electrically controlled to permit either type of gas to be admitted into output line 303. The gas in line 303 is split into two paths, one of which is connected to flow valve 305 and the other is connected to flow valve 306. The gas from flow valve 306 is passed from valve oven 30 via output line 14 to the upper portion of test cell 20. The gas from flow valve 305 is connected to a calibration valve 310, which can be set to either of two positions. In the position shown in FIG. 3, the test gas from flow valve 305 is coupled to an exhaust line 312. The carrier gas returned from test cell 20 is conveyed via line 29 to a cell valve 320. In the position shown on FIG. 3, cell valve 320 conveys the carrier gas to calibration valve 310, where it is conveyed from valve oven 30 via heated line 35. In the second position of cell valve 320, the carrier gas is conveyed from line 29 to an exhaust line 314. When valve 310 is in its second position the test gas from flow valve 305 is connected to exhaust 312, and the carrier gas return from test cell 20 is connected to heated line 35.

Figure 4:
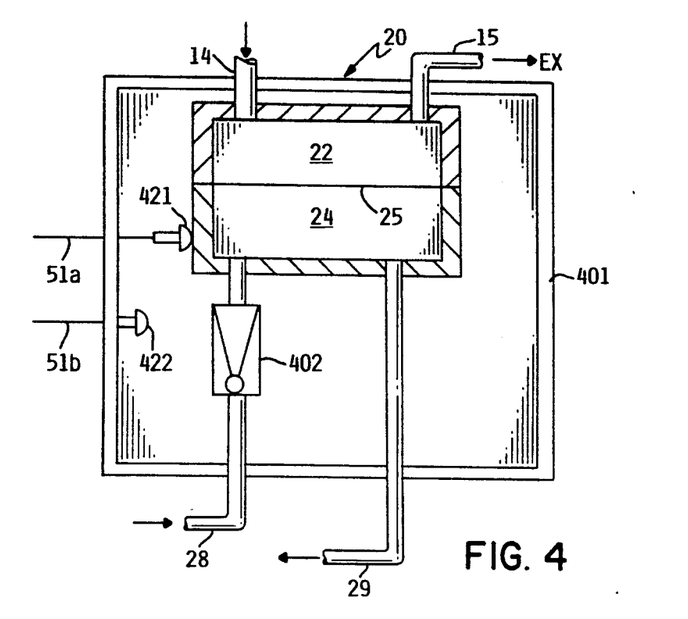
FIG. 4 shows the test cell of the present invention.

Referring next to FIG. 4, a diagram of the test cell 20 is shown. Test cell 20 includes insulated walls 401 to control the heat transfer therein. Test gas is admitted into an upper gas chamber 22 via line 14, and is exhausted (Ex) from upper gas chamber 22 via line 15. A carrier gas is admitted into a lower chamber 24 via line 28 and a flow valve 402, and is exhausted from lower chamber 24 via line 29. A barrier material 25 is clamped between the upper and lower chambers 22 and 24, to serve as the test material for measuring the permeability characteristics of the material 25. The interior of test cell 20 may have a heater (not shown) and temperature monitors 421 and 422 so as to precisely control the temperature within the test cell.

Figure 5:
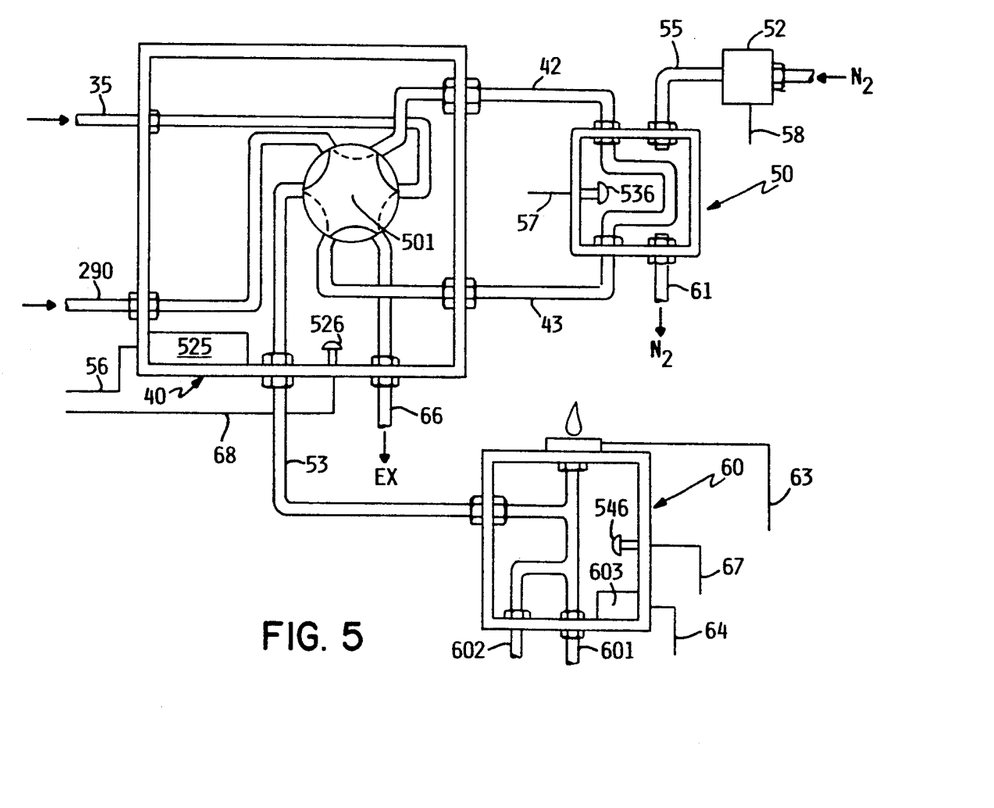
FIG. 5 shows the column oven, cryotrap, and flame ionization detector of the present invention.

FIG. 5 shows a schematic diagram of column oven 40, cryotrap 50, and flame ionization detector 60. Column oven 40 receives either a supply of carrier gas with organics via heated line 35 or pure carrier gas via line 290. An exam/collect valve 501 is contained within column oven 40, and is electrically selectable to either of two positions. The position shown in FIG. 5 is the "collection" position, wherein the carrier gas from line 35 is coupled to cryotrap 50 via line 42. The gas from cryotrap 50 is returned to column oven 40 via line 43. When the exam/collect valve is in its "exam" position the gas from heated line 35 is coupled to exhaust port 66, and the carrier gas via line 290 is coupled to output line 42 to cryotrap 50. The return gas from cryotrap 50 over line 43 is coupled to line 53 and flame ionization detector 60.

Flame ionization detector 60 has one input line 53 for receiving either a carrier gas from line 29 wherein the carrier gas passes through the cryotrap 50, where it picks up the concentrated organic molecules and carries them to the flame ionization detector (in the exam mode), or bypasses the cryotrap 50 and passes the gas directly into the flame ionization detector 60 (in the collect mode). In either case, flame ionization detector 60 has an input line 601 for receiving a supply of air, and an input line 602 for receiving a supply of hydrogen. Air and hydrogen are mixed with the carrier gas for burning within flame ionization detector 60, to determine the measurable characteristics of the gas under tests. The flame ionization detector may have a heater 603 controlled by line 64 and a temperature detector 546 monitored by line 67, which connects to controller 37 so as to control the temperature of the flame ionization detector 60. The signal current produced by the flame ionization detector is coupled to the electrometer 65 via line 63.

Figure 6:
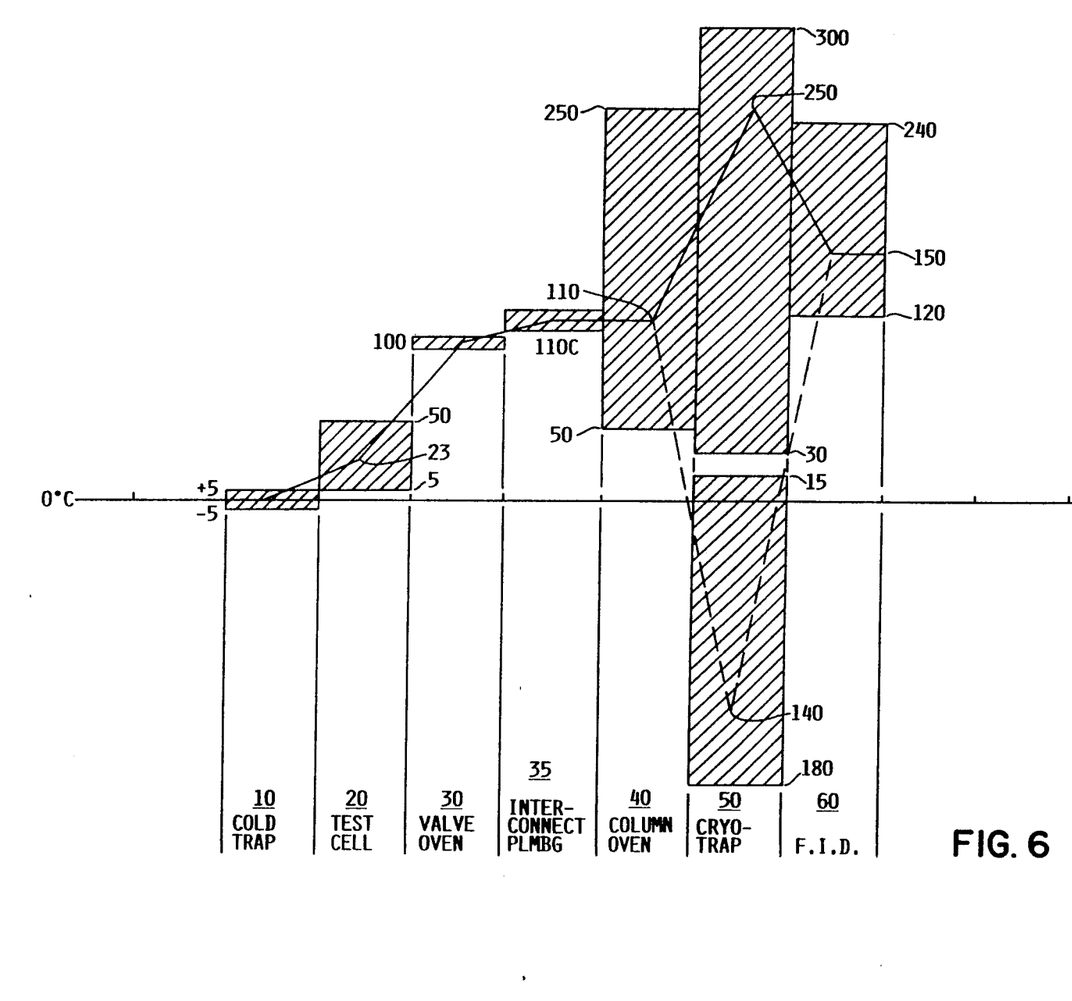
FIG. 6 shows a temperature profile of the present invention.

FIG. 6 shows the temperature control relationships between the various components of the system, and illustrates the respective temperature ranges for each component which must be maintained in order to maintain efficient operation of the system. All temperatures shown on FIG. 6 are referenced to a base line temperature of zero degrees Centigrade (0° C.), and the shaded portions of the figure indicate a range of temperatures over which a particular component may be controlled. The temperature within cold trap 10 is monitored by sensor 220, and the temperature is controlled to a range between $-5°$ C. to $+5°$ C. by selectively actuating electrical line 48, which controls solenoid valve 12 and regulates the amount of liquid nitrogen flowing through cold trap 10. Since liquid nitrogen entering cold trap 10 is at a temperature of approximately $-195°$ C., the solenoid flow control valve must be carefully regulated to allow only a small amount of liquid nitrogen to pass into cold trap 10.

The temperature of test cell 20 is controlled by a temperature bath (not shown), which is externally temperature regulated to a temperature range of +5° C. to 50° C. The actual temperature of test cell 20 is monitored by a temperature sensor within the test cell, which is electrically connected to controller 36 via line 51b.

The temperature within valve oven 30 is controlled by an internal electric heater 325, which is selectively actuated by driver 46. The temperature within valve oven 30 is monitored by temperature sensor 326 which is electrically connected to controller 36 via line 49a. The temperature within valve oven 30 is set to be greater than 100° C., to prevent contamination of the various gas lines within valve oven 30, and is typically controlled within a range slightly exceeding 100° C. The temperature of gas line 35, passing between ovens 30 and 40, is controlled by wrapping the gas lines with an electric heater tape. This heater tape is designed to maintain the temperature of the heated line above 105° C., and typically ranging between 105° C.–110° C.

The temperature of column oven 40 is controlled within the range of 50° C.–250° C., although for most testing cases it is held at a temperature exceeding 100° C. The temperature is controlled by an electric heater 525 within oven 40, which is actuated by driver 47 via line 56, and a temperature sensor 526 also within the valve oven, which is electrically coupled to controller 37. The electric heater and temperature sensor are connected to controller 47 via lines 56.

The temperature of cryotrap 50 is controllable over a very wide range, and is dependent upon the particular testing required. The temperature range is −190° C. to 300° C. The temperature is monitored by an internal temperature sensor 536, which is electrically connected to controller 37 via line 57. An internal heater (not shown) may be connected to driver 47 and be used to produce the elevated temperatures within cryotrap 50, and the lower temperatures are provided by the flow of liquid nitrogen through the cryotrap. The nitrogen flow is controlled by solenoid valve 52 via signals on line 58. The temperature of the flame ionization detector 60 is controlled within a range of 120° C.–300° C., and is nominally set at 150° C. This temperature must be maintained above 120° C. to prevent condensation, and the temperature should be greater than the oven 40 temperature. The temperature is controlled by a heater 603 actuated by driver 47 within the flame ionization detector, and is monitored by a temperature sensor 546 within the flame ionization detector 60, which is electrically connected to controller 37 via line 63.

Figure 7:
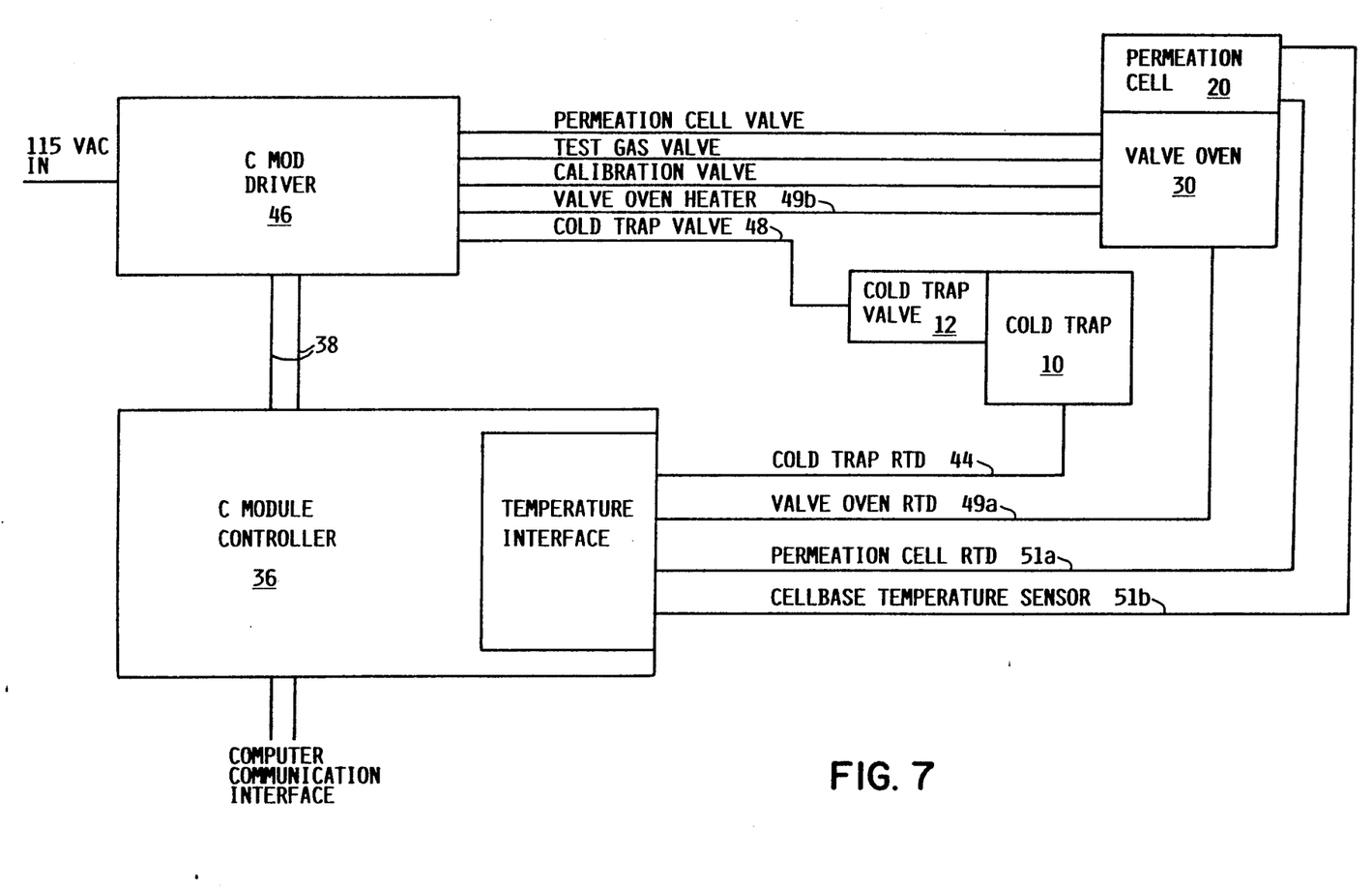
FIG. 7 shows a block diagram of one of the electronic control circuits of the present invention.

FIG. 7 shows a more detailed diagram of the electrical circuit modules associated with the invention. Controller 36 is a microprocessor-based semiconductor circuit which takes signal directions from an external computer over the computer interface lines, and returns the data and the status signals received from the sensors to the external computer over the same lines. Controller 36 controls the temperature of the cold trap 10 by receiving temperature-representative electrical signals from sensor 220 via line 44, and transmitting appropriate control signals to driver 46 via line 38, to control the cold trap solenoid valve 12. Controller 36 controls the temperature of the valve oven 30 by receiving temperature-representative electrical signals from temperature sensor 326 via line 49a, and by transmitting appropriate control signals to driver 46 via lines 38 to control an oven heater 325. Controller 36 also receives data from cell 20 temperature sensor 421 via line 51a, and sensor 422 via line 51b, and communicates these temperature signals to the remote computer for subsequent calculation and display. Controller 36 also receives data and instructions from the remote computer and utilizes these data and instructions to control a test sequence, by sending appropriate signals to driver 46 via lines 38, control cell valve 320, test gas valve 302 and calibration valve 310.

Figure 8:
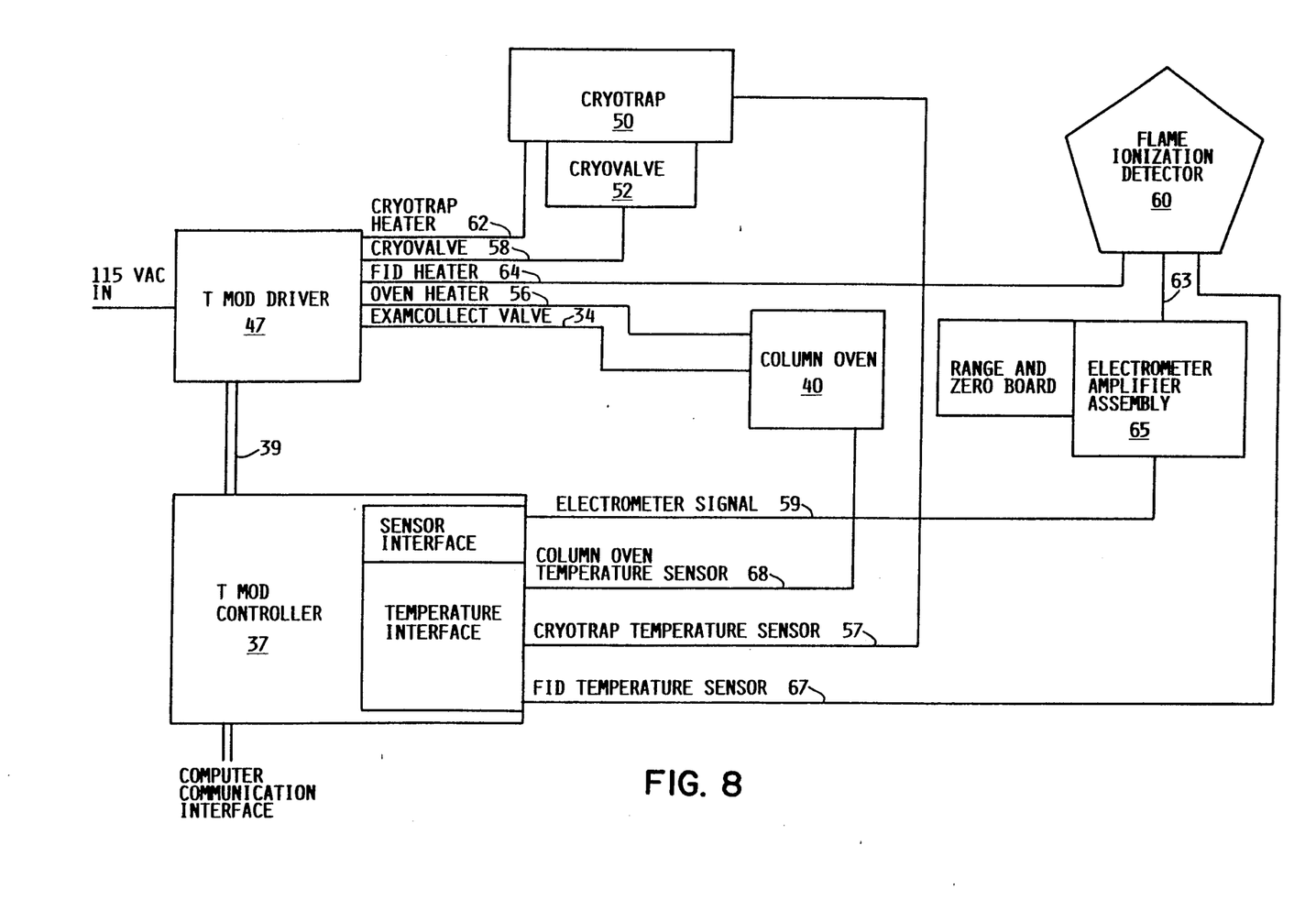
FIG. 8 shows a block diagram of another of the electronic control circuits of the invention.

FIG. 8 shows a more detailed diagram of the electronic circuit modules 37 and 47, illustrating the interface and control lines. Controller 37 is a microprocessor-based semiconductor circuit which takes directions from a remote computer over the computer interface lines, and returns data and status signals from the sensors. Controller 37 controls the temperature of the flame ionization detector 60 by receiving signals from the temperature sensor 546, and by sending appropriate control signals to driver 47 via lines 39 to control the flame ionization detector heater 603. Controller 37 controls the temperature of cryotrap 50 by receiving data from the cryotrap temperature sensor 536, and sending appropriate signals to driver 47 via lines 39 to control the cryotrap solenoid 52 or the cryotrap heater (not shown). Controller 37 controls the temperature of column oven 40 by receiving data from oven temperature sensor 526, and sending appropriate signals to driver 47 via lines 39 to control the oven heater 525.

The electrometer 65 continuously monitors the electronic signals from the flame ionization detector 60, and conditions, amplifies and transfers the signals to controller 37. Controller 37 then converts these signals and communicates the converted signals to the remote computer for quantification and display of the organic transmission rate. Controller 37 also receives data and instructions from the remote computer, and controls the test sequence of the system by sending appropriate signals to driver 47 via lines 39, to control the position of the "collect/exam" valve 501.

In operation, the invention is preferably used for detecting and measuring the transmission rate of volatile organic chemicals through a barrier material. A sample of the barrier material is clamped between the two half sections of the test cell, thereby separating the test cell into two chambers. The system is connected to a source of liquid nitrogen in order to provide the necessary cooling for the cold trap in the system, a source of hydrogen in order to provide the gas for burning in the flame ionization detector, an air source for assisting in the burning process in the flame ionization detector, a carrier gas source, preferably helium, for use during the test and measurement process, and a source of test gas containing the requisite organics for the particular type of test desired. The system valves are adjusted for each of the gases, and the test gas valve is set to permit approximately 15 cc per minute of test gas to flow through the system. Likewise, the carrier gas valves are set to permit approximately 15 cc's per minute of carrier gas to flow through the system. Hydrogen flow is set at approximately 10 cc per minute and air flow is set at approximately 350 cc per minute.

The system temperature controls are set to provide temperature set points for the various system components within the normal operating range of temperatures for each of the components. For example, the cold trap temperature is set to a set point of approximately 0° C.; controllable plumbing temperatures are set to approximately 100° C.; the cryotrap cold operating temperature is set to −170° C.; the cryotrap hot temperature control is set to +300° C.; the oven temperature is set to +250° C.; the flame ionization detector is set to +250° C.

The system is run through a calibration procedure as follows. The particular test gas selected for permeation testing is injected into the cryotrap, using precision injection devices, so that a known quantity of test gas may be evaluated. The test gas sample is examined by the flame ionization detector and readings are obtained which provide an indication of the quantity of organics residing in the test gas. The calibration procedure is preferably run a number of times so that a baseline may be established for the test gas to be later utilized in connection with the permeation testing.

After the calibration procedure has been completed the system is conditioned for a test cycle, by resetting the flow rates to approximately 15 cc per minute for the carrier and test gases. During the testing sequence the carrier and test gases are permitted to flow through the system, whereby a quantity of test gas may permeate through the test membrane from one of the chambers to the other, be picked up by the carrier gas, and conveyed throughout the remainder of the system. The carrier gas with the unknown quantity of organics is ultimately conveyed into the flame ionization detector where it is flamed, and the sensor associated with the flame ionization detector measures the quantities of the various gas components which may be present. This measurement is converted into a digital value and is ultimately conveyed to the remote computer processor. The remote computer processor may prepare suitable reports and display information for use by the operator, according to the requirements of the testing procedure.

The system is very amenable to total computer control using a remote processor and the microprocessors found on controllers 36 and 37. Software may be prepared which can control all aspects of the system, including cycle timing, valve controls and temperature controls. All of these operations may be controlled according to operator's instructions which may be input into the computer via an operator keyboard. Once the operating parameters have been set, the remote computer may control all components, control the gathering and logging of data from measurement devices, and make suitable presentations available for operator viewing in the form of the tables and/or bar charts on a display screen. Furthermore, the remote computer processor may collect and store data from tests for future reference.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. An apparatus for measuring the transmission rate of volatile organic chemicals through a barrier material, comprising:
   a) a test cell having means for clamping a barrier material sample between a first and second chamber;
   b) means for introducing a flow of test gas containing volatile organic chemicals into said first chamber;
   c) means for introducing a flow of carrier gas into said second chamber, and means for conveying gas from said second chamber;
   d) a cryotrap having means for connection to said means for conveying gas from said second chamber; and
   e) a flame ionization detector selectively coupled to said cryotrap, including means for measuring the organic chemicals collected in said cryotrap.

2. The apparatus of claim 1, further comprising means for heating said test cell to a first predetermined temperature.

3. The apparatus of claim 2, further comprising means for heating said means for conveying gas from said second chamber to a second predetermined temperature, higher than said first predetermined temperature.

4. The apparatus of claim 3, wherein said cryotrap further comprises means for cooling said gas to a temperature substantially below said second predetermined temperature.

5. The apparatus of claim 4, further comprising means, coupled to said flame ionization detector, for developing an electrical signal representative of said measurement of organic chemicals.

6. The apparatus of claim 5, further comprising data processing means for receiving said electrical signal and displaying said signal in readable form.

7. An apparatus for measuring the transmission rate of volatile organic chemicals through a barrier material, comprising:
   a) a test cell having means for clamping a barrier material sample between a first and second chamber;
   b) a gas conduit coupled into said first chamber, including means for selectively cooling the gas in said conduit to a first predetermined temperature;
   c) a carrier gas conduit coupled into said second chamber including means for selectively heating the gas in said second chamber to a second predetermined temperature, higher than said first temperature.
   d) an oven having means for heating to a third predetermined temperature, higher than said second temperature, and a carrier gas outlet conduit connected between said second chamber and said oven;
   e) a cryotrap having means for heating or cooling to a fourth predetermined temperature and a conduit connecting said cryotrap to said carrier gas outlet conduit; and
   f) a flame ionization detector connected to receive carrier gas from said cryotrap, whereby said flame ionization detector measures the volatile organic chemicals in said carrier gas.

8. The apparatus of claim 7, wherein said first predetermined temperature is between −5° C. and +5° C.

9. The apparatus of claim 8, wherein said second predetermined temperature is between +5° C. and +50° C.

10. The apparatus of claim 9, wherein said third predetermined temperature is between +50° C. and +250° C.

11. The apparatus of claim 10, wherein said fourth predetermined temperature is between −190° C. and +300° C.

12. The apparatus of claim 11, wherein said flame ionization detector further comprises means for burning a mixture of air, hydrogen and carrier gas.

13. The apparatus of claim 12, further comprising means for selectively setting the temperature of said flame ionization detector between +120° C. and +300° C.

* * * * *